(12) United States Patent
Goss et al.

(10) Patent No.: US 9,458,475 B2
(45) Date of Patent: Oct. 4, 2016

(54) CLAY IN ETHANOL PRODUCTION

(71) Applicant: Oil-Dri Corporation of America, Chicago, IL (US)

(72) Inventors: Robert G. Goss, Chicago, IL (US); Marc Herpfer, Chicago, IL (US); Laura Kajita, Chicago, IL (US); Yasmith Bernal, Chicago, IL (US)

(73) Assignee: OIL-DRI CORPORATION OF AMERICA, Chicago, IL (US)

( * ) Notice: Subject to any disclaimer, the term of this patent is extended or adjusted under 35 U.S.C. 154(b) by 0 days.

(21) Appl. No.: 14/049,932

(22) Filed: Oct. 9, 2013

(65) Prior Publication Data
US 2014/0141481 A1    May 22, 2014

Related U.S. Application Data

(60) Provisional application No. 61/711,263, filed on Oct. 9, 2012.

(51) Int. Cl.
*C12P 7/10* (2006.01)

(52) U.S. Cl.
CPC *C12P 7/10* (2013.01); *Y02E 50/16* (2013.01); *Y02E 50/17* (2013.01)

(58) Field of Classification Search
CPC ............ C12P 7/10; C12P 7/06; Y02E 50/16; Y02E 50/17
USPC ................................................ 435/161, 165
See application file for complete search history.

(56) References Cited

U.S. PATENT DOCUMENTS

| | | |
|---|---|---|
| 5,935,623 A | 8/1999 | Alonso-Debolt |
| 2007/0128334 A1 | 6/2007 | Pittman |
| 2007/0275446 A1 | 11/2007 | Lee |
| 2008/0020095 A1 | 1/2008 | Block et al. |
| 2012/0070516 A1 | 3/2012 | Tranquil et al. |

OTHER PUBLICATIONS

*Netafim Mesh* Vs. *Micron Comparison Chart* (2014) downloaded from http://www.netafimusa.com/files/literature/wastewater/Mesh-vs-Micron.pdf on Sep. 23, 2014.*
Tosun et al. Effect of Zeolite NaY and Ca-Montmorillonite on Ethanol Production Using Synthetic Molasses; Applied Biochemistry and Biotechnology, vol. 144 (2008) pp. 161-168.*
Garcia-Romero et al. On the Chemical Composition of Sepiolite and Palygorskite; Clays and Clay Minerals, vol. 58, No. 1 (2010) pp. 1-20.*
International Preliminary Report on Patentability and Written Opinion of the International Searching Authority dated Apr. 14, 2015, which issued during prosecution of International Application No. PCT/US2013/064114.

* cited by examiner

*Primary Examiner* — Scott Long
*Assistant Examiner* — Paul Martin
(74) *Attorney, Agent, or Firm* — Vedder Price P.C.; Deborah L. Lu; Mark W. Russell

(57) ABSTRACT

The present methods involves methods of improving ethanol production which may comprise the addition of clay during ethanol production.

15 Claims, 2 Drawing Sheets

CLAY IN ETHANOL PRODUCTION

RELATED APPLICATIONS AND INCORPORATION BY REFERENCE

This application claims benefit of and priority to U.S. provisional patent application Ser. No. 61/711,263 filed Oct. 9, 2012.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The present methods involves methods of improving ethanol production.

BACKGROUND OF THE INVENTION

Ethanol is by far the most widely produced renewable fuel in the United States and is contained in over 90% of the gasoline sold in the US.

The majority of the ethanol in the US is made from corn, but it also can be produced from other feedstocks.

The major steps in the dry mill process include milling (feedstock passes through a hammer mill, which grinds it into a fine powder), fermentation (enzymes, water and yeast are added to the mash, which is continually agitated and cooled until the ethanol concentration has been maximized), distillation (the fermented mash is pumped to the continuous flow, multi-column distillation system where the ethanol is removed from the solids and the water) and dehydration (alcohol is then dehydrated to 200 proof and the 200 proof alcohol is then pumped to a finished product tank).

After the ethanol is removed, the residue corn solids may be condensed and fed as is or dried to produce distillers dried grains with or without solubles (which may be collectively referred to as DDGS), a nutritious animal feed.

A byproduct of the above method includes toxins, which are undesirable in both the ethanol and DDGS. Furthermore, toxins that are found in the corn (or other feedstuff) is concentrated in the residue corn solids (such as DDGS) making it a problem to use in animal feeds.

Citation or identification of any document in this application is not an admission that such document is available as prior art to the present invention.

SUMMARY OF THE INVENTION

The present invention demonstrates that clay may increase the rate of ethanol production. The use of clay may decrease measured toxins (e.g., aflatoxin) in distillers dried grain with solubles (DDGS) if added upstream in the process. Clay may also increase enzyme activity. Clay may also reduce toxin presence (e.g., aflatoxin) in a fluid when combined with a feed material (e.g., DDGS or solubles), thus reducing bioavailability. It is contemplated that the clay binds to the toxin and by removing the clay, the toxin may also be removed.

The present invention relates to a method of increasing the rate of ethanol production which may comprise adding clay to whole corn, the slurry tank, the enzymes, the mash cooking and/or the fermentation steps of corn ethanol production, wherein the rate of ethanol production is increased when clay is added as compared to ethanol production when clay is not added.

The present invention relates to a method of decreasing measured toxins in distillers dried grain with solubles (DDGS), distillers dried grain (DDG) without solubles, and/or solubles which may comprise adding clay to whole corn, the slurry tank, the enzymes, the mash cooking and/or the fermentation steps of corn ethanol production, wherein the toxins are decreased when clay is added as compared to a method when clay is not added.

The present invention relates to a method of increasing enzyme activity during ethanol production which may comprise adding clay to an initial plant product from which ethanol is produced, the slurry tank, the enzymes, the mash cooking and/or the fermentation steps of ethanol production, wherein the enzyme activity is increased when clay is added as compared to enzyme activity when clay is not added.

The present invention relates to a method of reducing toxins in a fluid which may comprise combining a feed material with clay, wherein the toxins are reduced when clay is added as compared to a method when clay is not added.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product. Which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

The results are from the National Corn to Ethanol Research Center ("NCERC") on a lab scale.

DETAILED DESCRIPTION OF THE INVENTION

The present invention demonstrates that clay may increase the rate of ethanol production. The use of clay may decrease measured toxins (e.g., aflatoxin) in distillers dried grain with solubles ("DDGS") if added upstream in the process. Clay may also increase enzyme activity. Clay may also reduce toxin presence (e.g., aflatoxin) in a fluid when combined with a feed material (e.g., DDGS or solubles), thus reducing bioavailability. It is contemplated that the clay binds to the toxin and by removing the clay, the toxin may also be removed.

A number of clays are contemplated for the present invention, such as but not limited to, bentonite/montmorillonite clay, attapulgite/palygorskite clay and/or opalaceous material (opaline silica or Antelope shale) clay (also known as Blue Mountain, Georgia and Taft clays, respectively) as well as sepiolite, smectite, diatomaceous earth, activated carbon, organoclay, hydrous aluminosilicate, aluminosilicate, attapulgite/palygorskite, hormite, and bone ash.

As used herein, L-12-421 refers to a dried, less than 45 micron clay from Georgia (called Fullers Earth or attapulgite/palygorskite).

As used herein, L-12-422 is a dried, less than 150 micron clay from Mississippi (called bentonite/montmorillonite).

As used herein, L-12-423 is a dried and heat-treated less than 45 micron clay from Illinois (called bentonite/montmorillonite).

The clays of the present invention may be less than about 200 microns in size, advantageously less than 150 microns, advantageously less than 100 microns, advantageously less than 50 microns or advantageously less than 45 microns. The clay may be dried and/or heat treated.

The present invention also involves adding heat at between 300 and 800 degrees C. for up to an hour to the clay. The present invention also involves heating the clay, as it may impact the effectiveness of the clay. This may be done either statically using a muffle furnace or dynamically in a rotary kiln or flash dryer.

The clay constituent of the present compositions may be in the form of discrete particles. These particles may be angular or rounded. Although particle sizes up to about 1 inch are suitable, a preferred size of clay particles may be in the range of about 50 by about 400 mesh U.S. Sieve Series. For a tabulation of U.S. Sieve Series screen nomenclature, see Perry's Chemical Engineering Handbook, 6th Ed., McGraw-Hill, Inc., New York, N.Y. (1984), p 21-15 (table 21-6). An especially preferred size range for the clay particles in the present invention may be in the range of about 60 to about 325 mesh.

Figure 1:
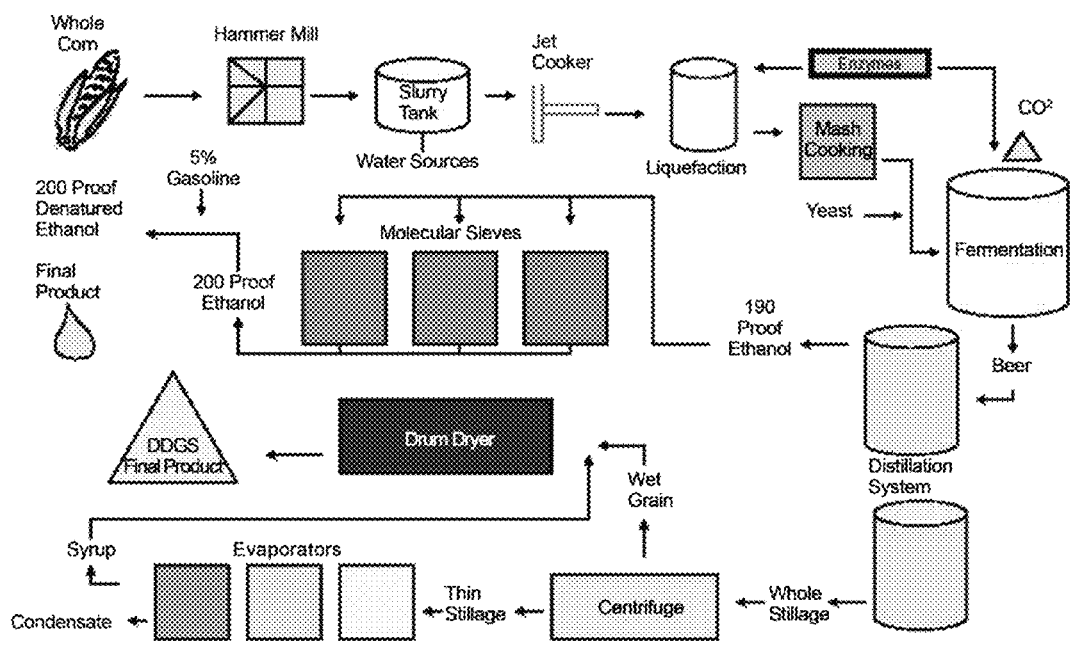
FIG. 1 depicts a dry milling ethanol production process.

FIG. 1 depicts a dry milling ethanol production process. The simplest use of the present invention may be to add clay after the hammer mill. In particular, the present invention contemplates adding clay to the whole corn, the slurry tank, the enzymes, the mash cooking and the fermentation steps as exemplified in FIG. 1.

The present invention contemplates adding clay to improve ethanol production and enzyme activity during production of corn ethanol. The present invention also contemplates adding clay to remove toxins during ethanol production. The addition of clay to dry milling and wet milling of ethanol production are contemplated.

Methods of producing corn ethanol are well known in the art (see, e.g., www.afdc.energy.gov and Goettemoeller, Jeffrey; Adrian Goettemoeller (2007). Sustainable Ethanol: Biofuels, Biorefineries, Cellulosic Biomass, Flex-Fuel Vehicles, and Sustainable Farming for Energy Independence. Prairie Oak Publishing, Maryville, Mo. p. 42).

The methods of the present invention may also be applied to the preparation of ethanol from not only corn but also algae, beets, cellulose waste, a polysaccharide source, potatoes, sorghum, sugarcane, switchgrass, vegetable waste and wood biomass.

Applicants have also found that clay may increase the rate of ethanol production. Therefore, the present invention also encompasses methods of increasing ethanol production by adding clay to the whole corn, the slurry tank, the enzymes, the mash cooking and the fermentation steps as exemplified in FIG. 1.

It is contemplated about 0.1% (w/w) to about 5% (w/w), advantageously about 0.5% (w/w) to about 2% (w/w) of the clay (as compared to the weight of the end product of ethanol production, such as distillers dried grain with solubles ("DDGS").

Figure 2:
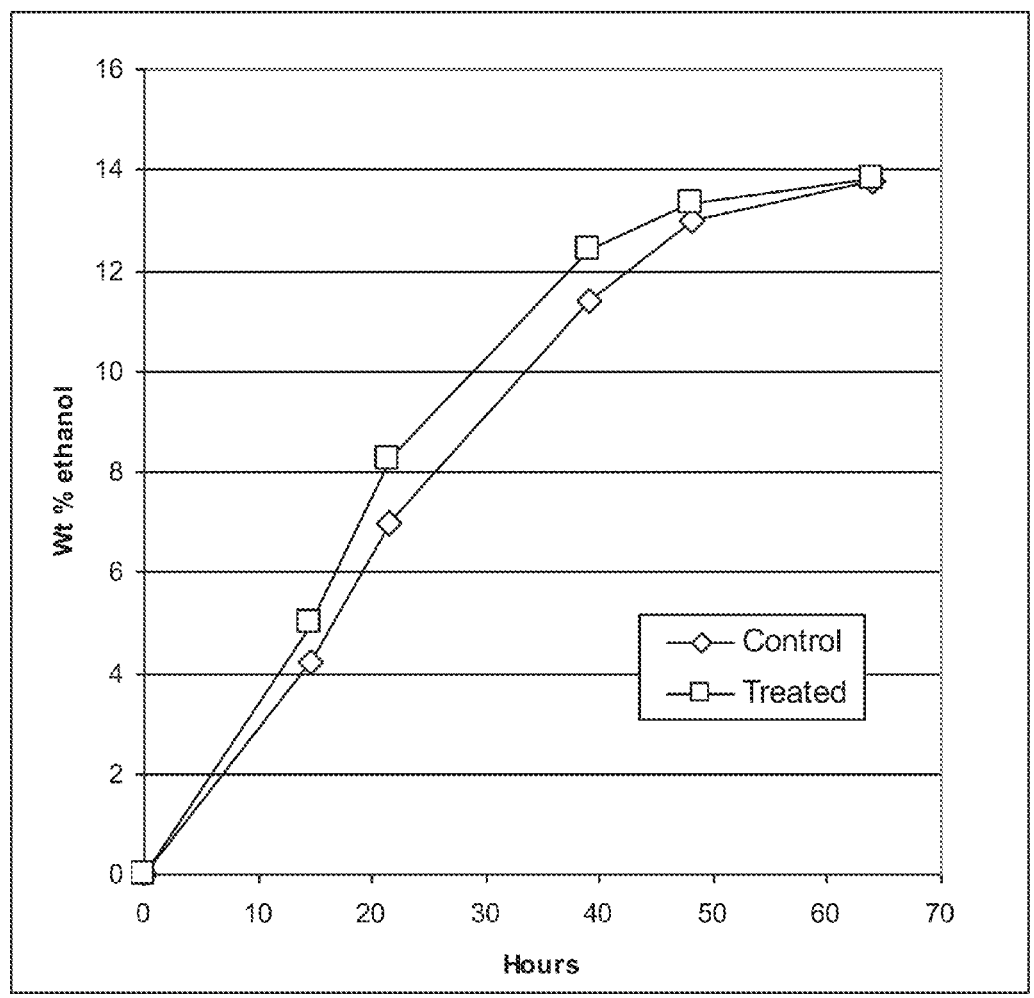
FIG. 2 depicts addition of L-11-422 2% of DDGS (0.67% of corn feedstock) added to alpha-amylase enzyme solution.

FIG. 2 depicts addition of L-12-422 2% of DDGS (0.67% of corn feedstock) added to alpha-amylase enzyme solution. The results are from the National Corn to Ethanol Research Center ("NCERC") on a lab scale.

The present invention also contemplates addition of clay to an end product of ethanol production, such as DDGS to remove toxins. Advantageously about 0.1% (w/w) to about 5% (w/w), advantageously about 0.5% (w/w) to about 2% (w/w) of the clay (as compared to the weight of the end product of ethanol production, such as DDGS). It is contemplated that DDGS may be about 0.1% (w/w) to about 1% (w/w) of clay in the feedstock, advantageously about 0.67% (w/w) of clay in the feedstock.

Clay may greatly lessen measured aflatoxin in DDGS if added to the "fermentation tank" (i.e., mash Table 1). Results are from lab fermentations and aflatoxin analyses were performed.

Therefore, the present invention also contemplates the removal of toxins that were in the initial feedstock or produced during ethanol production by adding clay to the whole corn, the slurry tank, the enzymes, the mash cooking and the fermentation steps as exemplified in FIG. 1. It is contemplated that the clay binds toxins and removal of the clay from the ethanol production process also removes the toxins.

TABLE 1

Measured aflatoxin in DDGS after fermentation, L-12-423 added at a rate of 2% of DDGS (0.67% of corn feedstock) in mash.

| NCERC | | Aflatoxin Presence in DDGS (ppb) | |
| --- | --- | --- | --- |
| Project | Initial corn | Untreated | Treated |
| A | 328 | 666 | 17.8 |
| B | 234 | 231 | 8.8 |

The initial investigation looked at the effect of clay on fermentation, the effect of aflatoxin on fermentation, and the effect of clay on measured aflatoxin in DDGS. Clay was added in the "fermentation tank" (i.e., the mash having a 25% concentration from FIG. 1). Aflatoxin is concentrated in the DDGS, but not to the anticipated 3× level. Addition of Oil-Dri materials (L-12-421, -422 and -423) to the mash greatly reduced measured aflatoxin in the DDGS. Included in the experiment was an uncontaminated corn sample. The presence of aflatoxin did not affect ethanol production.

TABLE 2

Measured aflatoxin in DDGS after fermentation, clay added in mash.

| Treatment | Addition Level (% of DDGS) | Aflatoxin in DDGS (ppb) |
|---|---|---|
| Initial corn | | 327.5 |
| Untreated | | 665.5 |
| L-12-421 | 0.5 | 251.7 |
| L-12-421 | 2.0 | 68.1 |
| L-12-422 | 0.5 | 305.9 |
| L-12-422 | 2.0 | 78.3 |
| L-12-423 | 0.5 | 89.0 |
| L-12-423 | 2.0 | 17.8 |

A second experiment investigated the effects of clay on fermentation, the effect of aflatoxin on fermentation, the effect of clay on measured aflatoxin in DDGS, the effect of adding clay to DDGS on measured aflatoxin, the effect of adding clay to a feed material on a stimulated stomach digestive juice, and the effect of adding clay to condensed solubles on measured aflatoxin.

Both ethanol production rate and ethanol yield were slightly increased.

Table 3 shows the effect of adding 2% clay to DDGS and performing an aflatoxin measurement. There is no effect on measured aflatoxin.

TABLE 3

Aflatoxin (ppb) in corn and DDGS.

| Analyte | DDGS | DDGS + L-12-421 | DDGS + L-12-422 | DDGS + L-12-423 |
|---|---|---|---|---|
| Aflatoxin | 341.5 | 321.1 | 334.3 | 306.8 |

If clay is added in the "fermentation tank", we see a greatly reduced measured aflatoxin level (Table 4). The measured aflatoxin in the DDGS had not increased from the initial aflatoxin content in the feedstock corn, which is unusual. Clay must be added upstream in the process to affect measured aflatoxin.

TABLE 4

Measured aflatoxin in DDGS after fermentation, clay added in mash.

| Treatment | Addition Level (% of DDGS) | Aflatoxin in DDGS (ppb) |
|---|---|---|
| Initial corn | | 230.5 |
| DDGS | | 231 |
| L-12-421 | 0.5 | 169 |
| L-12-421 | 2.0 | 24 |
| L-12-422 | 0.5 | 104 |
| L-12-422 | 2.0 | 24 |
| L-12-423 | 0.5 | 21 |
| L-12-423 | 2.0 | 9 |

To measure the effect of adding clay to condensed solubles (syrup from FIG. 1), Applicants spiked aflatoxin into condensed solubles obtained from a commercial source. To this condensed solubles was added various clay materials. Table 5 shows measured aflatoxin was greatly lessened.

TABLE 5

Aflatoxin binding in solidified condensed solubles.

| SAMPLE | Aflatoxin Assay (ppb) |
|---|---|
| Commercial Plant Condensed Solubles | ND |
| Spiked Condensed Solubles | 236 |
| Solidified Spiked Solubles Granular heated treated bentonite/montmorillonite | 5 |
| Solidified Spiked Solubles <60 mesh dried bentonite/montmorillonite | 7 |
| Solidified Spiked Solubles <325 mesh dried attapulgite/palygorskite clay | 47 |

As another part of experiment 2, Applicants examined aflatoxin presence with or without clay in either DDGS or condensed solubles in a simulated fluid. This would mimic what an animal would experience on eating the material. Applicants added test materials to either DDGS or condensed solubles, placed the material in an aqueous solution designed to simulate a stomach fluid (concentrate is ~2.35 ml glacial acetic acid (0.150 M) (2.25 g), 5.20 g $NaH_2PO_4 \cdot H_2O$ (0.150 M), 1.10 g NaCl (0.075 M), 1.42 g KCl (0.075 M), $H_2O$ and NaOH pH 2.8, $H_2O$ to 250 ml). For a test, dilute the concentration by 1:2 (one part stomach fluid to two parts water), and analyzed for the presence of toxin in the supernatant (i.e., the simulated stomach fluid). Addition of 2% of a clay lessened detected aflatoxin in all cases (Table 6).

TABLE 6

Presence of aflatoxin in a simulated stomach fluid.

| Test Material, | ppb Aflatoxin | |
|---|---|---|
| added at @5 wt/wt | DDGS | Condensed Solubles |
| None | 2.6 | 16.5 |
| L-12-421 | ND | ND |
| L-12-422 | ND | ND |
| L-12-423 | ND | ND |

In a third experiment, Applicants focused on fermentation only. Applicants did not use aflatoxin contaminated corn. Applicants reproduced industrial fermentation conditions as closely as possible (32% mash) and measured total ethanol production, fermentation rate, and various enzyme activity rates. Applicants added clay to either the whole corn (see FIG. 1) or to the alpha-amylase enzyme diluted solution (enzymes from FIG. 1). Clay had a positive effect on both fermentation rate (Table 7) and enzyme activity (Table 8). The highest fermentation rate was achieved with 2% of DDGS (0.67% of corn feedstock) added to the alpha-amylase enzyme solution.

TABLE 7

Fermentation rates.

| | % alcohol Time (hours) | | | | | |
|---|---|---|---|---|---|---|
| Treatment (% of DDGS) | 0 | 14.5 | 21.5 | 39 | 48 | 64 |
| Control | 0.00 | 4.21 | 6.96 | 11.38 | 13.01 | 13.76 |
| 0.5% L-12-421 in corn | 0.00 | 4.62 | 7.15 | 11.73 | 13.01 | 13.63 |

TABLE 7-continued

Fermentation rates.

| Treatment (% of DDGS) | % alcohol Time (hours) | | | | | |
|---|---|---|---|---|---|---|
| | 0 | 14.5 | 21.5 | 39 | 48 | 64 |
| 2% L-12-421 in corn | 0.00 | 4.56 | 6.84 | 11.16 | 12.72 | 13.63 |
| 0.5% L-12-422 in corn | 0.00 | 4.55 | 7.21 | 11.58 | 13.01 | 13.57 |
| 2% L-12-422 in corn | 0.00 | 4.71 | 7.40 | 11.72 | 13.06 | 13.60 |
| 0.5% L-12-423 in corn | 0.00 | 4.82 | 7.66 | 12.22 | 13.14 | 13.75 |
| 2% L-12-423 in corn | 0.00 | 4.78 | 7.59 | 12.08 | 13.18 | 13.70 |
| 0.5% L-12-421 in enzyme | 0.00 | 4.83 | 7.38 | 11.76 | 12.56 | 13.47 |
| 2% L-12-421 in enzyme | 0.00 | 4.87 | 7.38 | 11.61 | 13.04 | 13.76 |
| 0.5% L-12-422 in enzyme | 0.00 | 4.77 | 7.68 | 12.07 | 13.27 | 13.95 |
| 2% L-12-422 in enzyme | 0.00 | 4.98 | 8.25 | 12.39 | 13.32 | 13.81 |
| 0.5% L-12-423 in enzyme | 0.00 | 4.72 | 7.69 | 12.17 | 13.26 | 13.83 |
| 2% L-12-423 in enzyme | 0.00 | 4.73 | 7.75 | 12.44 | 13.24 | 13.81 |

TABLE 8

Enzyme activity, glucose levels during liquefaction

| Treatment (% of DDGS) | Glucose Levels During Liquefaction (%, w/v) | | |
|---|---|---|---|
| | 30 Minutes | 60 Minutes | 90 Minutes |
| Control (No Clay) | 0.63 | 0.63 | 0.66 |
| 0.5% L-12-421 in corn | 0.67 | 0.68 | 0.67 |
| 2% L-12-421 in corn | 0.7 | 0.66 | 0.66 |
| 0.5% L-12-422 in corn | 0.69 | 0.7 | 0.68 |
| 2% L-12-422 in corn | 0.75 | 0.72 | 0.75 |
| 0.5% L-12-423 in corn | 0.6 | 0.74 | 0.76 |
| 2% L-12-423 in corn | 0.75 | 0.75 | 0.77 |
| 0.5% L-12-421 in enzyme | 0.73 | 0.77 | 0.86 |
| 2% L-12-421 in enzyme | 0.78 | 0.81 | 0.86 |
| 0.5% L-12-422 in enzyme | 0.6 | 0.7 | 0.72 |
| 2% L-12-422 in enzyme | 0.68 | 0.69 | 0.75 |
| 0.5% L-12-423 in enzyme | 0.67 | 0.7 | 0.74 |
| 2% L-12-423 in enzyme | 0.66 | 0.69 | 0.69 |

Corn may have a high aflatoxin content due to growing conditions. Research has shown an increase in the rate of ethanol production with the materials of the present invention. If used upstream in the process, the materials of the present invention may significantly lessen measured aflatoxin in one of the ethanol production byproducts, DDGS, that is sold into the animal feed industry.

The invention also contemplates methods of decreasing measured toxins in distillers dried grain with solubles (DDGS) and/or solubles which may comprise adding a non-clay toxin binder to whole corn, the slurry tank, the enzymes, the mash cooking and/or the fermentation steps of corn ethanol production, wherein the toxins are decreased when the non-clay toxin binder is added as compared to a method when the non-clay toxin binder is not added.

In one embodiment, the non-clay toxin binder may be a polysaccharide, such as a glucan, a mannan or a chitin. The glucan may be a β-D glucan, such as a β-(1,3)-D glucan or a β-(1,6)-D glucan. In another embodiment, the non-clay toxin binder may be a yeast cell wall or a fragment thereof (such as proteins, lipids and inorganic phosphate).

Although the present invention and its advantages have been described in detail, it should be understood that various changes, substitutions and alterations can be made herein without departing from the spirit and scope of the invention as defined in the appended claims.

The invention is further described by the following numbered paragraphs:

1. A method of increasing the rate of ethanol production comprising adding clay to whole corn, the slurry tank, the enzymes, the mash cooking and/or the fermentation steps of corn ethanol production, wherein the rate of ethanol production is increased when clay is added as compared to ethanol production when clay is not added.

2. A method of decreasing measured toxins in distillers dried grain with solubles (DDGS), distillers dried grain (DDG) without solubles, and/or solubles comprising adding clay to whole corn, the slurry tank, the enzymes, the mash cooking and/or the fermentation steps of corn ethanol production, wherein the toxins are decreased when clay is added as compared to a method when clay is not added.

3. A method of increasing enzyme activity during ethanol production comprising adding clay to an initial product from which ethanol is produced, the slurry tank, the enzymes, the mash cooking and/or the fermentation steps of ethanol production, wherein the enzyme activity is increased when clay is added as compared to enzyme activity when clay is not added.

4. A method of reducing toxins in a fluid comprising combining a feed material with clay, wherein the toxins are reduced when clay is added as compared to a method when clay is not added.

5. The method of any one of paragraphs 1-4, wherein the clay is Bentonite/montmorillonite clay, attapulgite/palygorskite clay or opalaceous material (opaline silica or Antelope shale) clay (also known as Blue Mountain, Georgia and Taft clays, respectively).

6. The method of paragraph 5, wherein the clay is an attapulgite/palygorskite clay.

7. The method of paragraph 5, wherein the clay is a bentonite/montmorillonite clay.

8. The method of any one of paragraphs 1-7, wherein the clay is less than 45 microns.

9. The method of any one of paragraphs 1-8, wherein the clay is less than 150 microns.

10. The method of any one of paragraphs 1-9, wherein the clay is dried.

11. The method of any one of paragraphs 1-10, wherein the clay is heat treated.

12. The method of any one of paragraphs 1-3 or 5-11, wherein the clay comprises a size range of about 4 to about 325 mesh.

13. The method of any one of paragraphs 1-3 or 5-12, wherein the clay is added to the initial product as exemplified in FIG. 1.

14. The method of any one of paragraphs 1-3 or 5-13, wherein the clay is added to the slurry tank as exemplified in FIG. 1.

15. The method of any one of paragraphs 1-3 or 5-14, wherein the clay is added to the enzymes as exemplified in FIG. 1.

16. The method of any one of paragraphs 1-3 or 5-15, wherein the clay is added to the mash cooking as exemplified in FIG. 1.

17. The method of any one of paragraphs 1-16, wherein about 0.1% (w/W) to about 5% (w/w), advantageously about 0.5% (w/w) to about 2% (w/w) of the clay (as compared to the weight of an end product of ethanol production, such as DDGS) is added.

18. The method of paragraph 17, wherein about 0.5% (w/w) to about 2% (w/w) of the clay (as compared to the weight of an end product of ethanol production, such as DDGS) is added.

19. The method of any one of claims 3-18, wherein the initial plant product is corn.

20. The method of any one of paragraphs 2 or 4-18, wherein the method further comprises removing the clay.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method of increasing the rate of ethanol production comprising adding clay to an initial plant product, the slurry tank, the enzymes, the mash cooking and/or the fermentation steps of corn ethanol production at about 0.1% (w/w) to about 5% (w/w) of the clay as compared to the estimated weight of distillers dried grain with solubles (DDGS) as compared to a method when clay is not added to an initial plant product, the slurry tank, the enzymes, the mash cooking and/or the fermentation steps of corn ethanol production, wherein the clay is dried and heat-treated from 300° C. to 800° C., wherein the rate of ethanol production is increased when clay is added as compared to ethanol production when clay is not added.

2. The method of claim 1, wherein the clay is bentonite/montmorillonite clay, attapulgite/palygorskite clay or opalaceous material (opaline silica or Antelope shale) clay (also known as Blue Mountain, Georgia and Taft clays, respectively).

3. The method of claim 2, wherein the clay is an attapulgite/palygorskite clay.

4. The method of claim 2, wherein the clay is a bentonite/montmorillonite clay.

5. The method of claim 1, wherein the clay is less than 45 microns.

6. The method of claim 1, wherein the clay is less than 150 microns.

7. The method of claim 1, wherein the clay comprises a size range of about 4 to about 325 mesh.

8. The method of claim 1, wherein the clay is added to an initial plant product.

9. The method of claim 1, wherein the clay is added to the slurry tank as exemplified in FIG. 1.

10. The method of claim 1, wherein the clay is added to the enzymes as exemplified in FIG. 1.

11. The method of claim 1, wherein the clay is added to the mash cooking as exemplified in FIG. 1.

12. The method of claim 1, wherein about 0.5% (w/w) to about 2% (w/w) of the clay (as compared to the weight of DDGS) is added.

13. The method of claim 1, wherein the initial plant product is corn.

14. The method of claim 1, wherein the method further comprises removing the clay.

15. A method of decreasing measured toxins in distillers dried grain with solubles (DDGS), comprising adding clay to an initial plant product, the slurry tank, the enzymes, the mash cooking and/or the fermentation steps of corn ethanol production, wherein the toxins are decreased when clay is added at about 0.1% (w/w) to about 5% (w/w) of the clay (as compared to the estimated weight of DDGS) as compared to a method when clay is not added.

* * * * *